US010675173B2

(12) United States Patent
Thorsteinsdottir et al.

(10) Patent No.: US 10,675,173 B2
(45) Date of Patent: *Jun. 9, 2020

(54) CERVICAL COLLAR

(71) Applicant: OSSUR HF, Reykjavik (IS)

(72) Inventors: Hildur Inga Thorsteinsdottir, Reykjavik (IS); Arni Thor Ingimundarson, Reykjavik (IS)

(73) Assignee: OSSUR HF, Reykjavik (IS)

( * ) Notice: Subject to any disclaimer, the term of this patent is extended or adjusted under 35 U.S.C. 154(b) by 324 days.

This patent is subject to a terminal disclaimer.

(21) Appl. No.: 15/598,524

(22) Filed: May 18, 2017

(65) Prior Publication Data

US 2017/0252198 A1    Sep. 7, 2017

Related U.S. Application Data

(63) Continuation of application No. 13/896,961, filed on May 17, 2013, now Pat. No. 9,713,546.

(60) Provisional application No. 61/649,615, filed on May 21, 2012.

(51) Int. Cl.
*A61F 5/055* (2006.01)
*A61F 5/058* (2006.01)
*A61F 5/05* (2006.01)

(52) U.S. Cl.
CPC ............... *A61F 5/055* (2013.01); *A61F 5/05* (2013.01); *A61F 5/05883* (2013.01)

(58) Field of Classification Search
CPC .................... A61F 5/055; A61F 5/05883
USPC ..... 602/18; 24/455, 489, 494, 498, 517, 519
See application file for complete search history.

(56) References Cited

U.S. PATENT DOCUMENTS

| 2,088,207 A | 7/1937 | Kaiser |
| 2,102,069 A | 12/1937 | Hanicke |
| 2,735,424 A | 2/1953 | Benjamin |
| 2,791,999 A | 5/1954 | Bustamante |
| 2,801,630 A | 8/1957 | Moore |
| 2,806,063 A | 9/1957 | Rigterink et al. |

(Continued)

FOREIGN PATENT DOCUMENTS

| CN | 1646071 A | 7/2005 |
| CN | 2933343 Y | 8/2007 |

(Continued)

OTHER PUBLICATIONS

Partial International Search Report from PCT Application No. PCT/US2017/050206, dated Dec. 5, 2017.

(Continued)

*Primary Examiner* — Keri J Nelson
(74) *Attorney, Agent, or Firm* — Workman Nydegger

(57) ABSTRACT

A cervical collar has a chin support slidably connected to an inside surface of an anterior component adapted to secure against an anterior chin and neck of a user. A posterior component connects to the anterior component to circumferentially surround the user's neck. A height adjustment mechanism has spring locks securing the height adjustment mechanism against the anterior component. The cervical collar includes a footplate continuously extending from the height adjustment mechanism generally without a variation in thickness. The posterior component has side portions with a plurality of living hinges located proximate to elongate slots for straps connecting to the anterior component.

17 Claims, 8 Drawing Sheets

(56) References Cited

U.S. PATENT DOCUMENTS

| | | |
|---|---|---|
| 2,806,471 A | 11/1957 | Breese |
| 2,818,063 A | 12/1957 | Smith et al. |
| 2,820,455 A | 1/1958 | Hall |
| 2,911,970 A | 11/1959 | Bartels |
| D188,302 S | 6/1960 | Monfardini |
| 3,024,784 A | 3/1962 | Monfardini |
| 3,027,894 A | 4/1962 | Moore |
| 3,042,027 A | 7/1962 | Monfardini |
| 3,050,052 A | 8/1962 | Grassl |
| 3,060,930 A | 10/1962 | Grassl |
| 3,075,521 A | 1/1963 | Grassl |
| 3,135,256 A | 6/1964 | Gruber |
| 3,177,869 A | 4/1965 | Bartels |
| D203,018 S | 11/1965 | Helferich |
| 3,285,243 A | 11/1966 | Yellin |
| 3,285,244 A | 11/1966 | Cottrell |
| 3,306,284 A | 2/1967 | McKinley |
| 3,313,297 A | 4/1967 | Applegate et al. |
| 3,320,950 A | 5/1967 | McElvenny |
| 3,504,667 A | 4/1970 | McFarlane |
| 3,512,523 A | 5/1970 | Barnett |
| 3,756,226 A | 9/1973 | Calabrese et al. |
| 3,916,884 A | 11/1975 | Attenburrow |
| 3,916,885 A | 11/1975 | Gaylord, Jr. |
| 4,099,523 A | 7/1978 | Lowrey |
| 4,173,973 A | 11/1979 | Hendricks |
| 4,205,667 A | 6/1980 | Gaylord, Jr. |
| 4,325,363 A | 4/1982 | Berkeley |
| 4,401,111 A | 8/1983 | Blackstone |
| 4,413,619 A | 11/1983 | Garth |
| D278,747 S | 5/1985 | Peach, Jr. |
| 4,520,801 A | 6/1985 | Lerman |
| 4,538,597 A | 9/1985 | Lerman |
| 4,562,833 A | 1/1986 | Pujals, Jr. |
| 4,582,051 A | 4/1986 | Greene et al. |
| 4,628,913 A | 12/1986 | Lerman |
| 4,643,174 A | 2/1987 | Horiuchi |
| 4,677,969 A | 7/1987 | Calabrese |
| 4,702,233 A | 10/1987 | Omicioli |
| 4,708,129 A | 11/1987 | Pujals, Jr. |
| 4,712,540 A | 12/1987 | Tucker et al. |
| 4,732,144 A | 3/1988 | Cunanan |
| 4,745,922 A | 5/1988 | Taylor |
| 4,827,915 A | 5/1989 | Gorsen |
| 4,854,306 A | 8/1989 | Pujals, Jr. |
| 4,886,052 A | 12/1989 | Calabrese |
| 4,940,043 A | 7/1990 | Burns et al. |
| 4,955,368 A | 9/1990 | Heimann |
| 4,987,891 A | 1/1991 | Gaylord, Jr. et al. |
| D314,623 S | 2/1991 | Calabrese et al. |
| 5,005,563 A | 4/1991 | Veale |
| 5,038,759 A | 8/1991 | Morgenstern |
| 5,058,572 A | 10/1991 | Schmid et al. |
| 5,060,637 A | 10/1991 | Schmid et al. |
| 5,097,824 A | 3/1992 | Garth |
| 5,156,588 A | 10/1992 | Marcune et al. |
| 5,180,361 A | 1/1993 | Moore et al. |
| 5,201,702 A | 4/1993 | Mars |
| 5,215,517 A | 6/1993 | Stevenson et al. |
| 5,230,698 A | 7/1993 | Garth |
| 5,275,581 A | 1/1994 | Bender |
| 5,302,170 A | 4/1994 | Tweardy |
| RE34,714 E | 8/1994 | Burns et al. |
| 5,346,461 A | 9/1994 | Heinz et al. |
| 5,366,438 A | 11/1994 | Martin, Sr. |
| 5,385,535 A | 1/1995 | McGuinness |
| 5,433,696 A | 7/1995 | Osti |
| 5,437,612 A | 8/1995 | Moore et al. |
| 5,437,617 A | 8/1995 | Heinz et al. |
| 5,445,602 A | 8/1995 | Grim et al. |
| D368,527 S | 4/1996 | Brooke |
| D369,660 S | 5/1996 | Myoga |
| 5,520,619 A | 5/1996 | Martin |
| RE35,290 E | 7/1996 | Druskoczi |
| 5,588,957 A | 12/1996 | Martin, Sr. |
| 5,593,382 A | 1/1997 | Rudy, Jr. et al. |
| 5,622,529 A | 4/1997 | Calabrese |
| 5,624,387 A | 4/1997 | McGuinness |
| D379,232 S | 5/1997 | Brooke |
| 5,632,722 A | 5/1997 | Tweardy et al. |
| 5,688,229 A | 11/1997 | Bauer |
| 5,716,335 A | 2/1998 | Iglesias et al. |
| 5,728,054 A | 3/1998 | Martin |
| D393,718 S | 4/1998 | Traut et al. |
| 5,785,670 A | 7/1998 | Hiebert |
| 5,788,658 A | 8/1998 | Islava |
| 5,795,315 A | 8/1998 | Traut et al. |
| 5,797,713 A | 8/1998 | Tweardy et al. |
| 5,797,863 A | 8/1998 | Kohnke |
| RE35,940 E | 10/1998 | Heinz et al. |
| 5,865,773 A | 2/1999 | Koledin |
| 5,904,662 A | 5/1999 | Myoga |
| 5,934,599 A | 8/1999 | Hammerslag |
| 5,947,666 A * | 9/1999 | Huang ............... B60P 7/15 410/143 |
| 5,964,722 A | 10/1999 | Goralnik et al. |
| 5,976,098 A | 11/1999 | Sereboff |
| 5,993,403 A | 11/1999 | Martin |
| 6,027,467 A | 2/2000 | Nakamura et al. |
| 6,036,664 A | 3/2000 | Martin, Sr. et al. |
| D422,710 S | 4/2000 | Maynard |
| 6,045,522 A | 4/2000 | Grober |
| 6,045,523 A | 4/2000 | Donaldson |
| 6,050,965 A | 4/2000 | Pillai |
| 6,056,711 A | 5/2000 | Domamski et al. |
| 6,058,517 A | 5/2000 | Hartunian |
| RE36,745 E | 6/2000 | Rudy, Jr. et al. |
| 6,071,255 A | 6/2000 | Calabrese |
| 6,071,256 A | 6/2000 | Lam |
| 6,090,058 A | 7/2000 | Traut et al. |
| 6,165,146 A | 12/2000 | Giebeler |
| 6,183,501 B1 | 2/2001 | Latham |
| 6,202,953 B1 | 3/2001 | Hammerslag |
| 6,245,033 B1 | 6/2001 | Martin |
| 6,254,560 B1 | 7/2001 | Tweardy et al. |
| 6,308,345 B1 | 10/2001 | Williams, Jr. |
| 6,289,558 B1 | 11/2001 | Hammerslag |
| 6,315,746 B1 | 11/2001 | Garth et al. |
| 6,423,020 B1 | 7/2002 | Koledin |
| 6,458,090 B1 | 10/2002 | Walpin |
| 6,494,854 B1 | 12/2002 | Visness et al. |
| D475,139 S | 5/2003 | Myoga |
| 6,632,722 B2 | 10/2003 | Fujiwara et al. |
| 6,663,581 B1 | 12/2003 | Calabrese |
| 6,663,630 B2 | 12/2003 | Farley et al. |
| 6,726,643 B1 | 4/2004 | Martin |
| 6,733,469 B2 | 5/2004 | Miyaji et al. |
| 6,740,055 B2 | 5/2004 | Dominguez |
| 6,770,046 B2 | 8/2004 | Hansen |
| 6,872,188 B2 | 3/2005 | Caille et al. |
| 6,913,584 B2 | 7/2005 | Rudy, Jr. et al. |
| 6,921,376 B2 | 7/2005 | Tweardy et al. |
| 6,926,686 B2 | 8/2005 | Cheatham |
| 7,018,351 B1 | 3/2006 | Iglesias et al. |
| 7,041,073 B1 | 5/2006 | Patron |
| 7,070,573 B2 | 7/2006 | Axelsson |
| 7,090,652 B2 | 8/2006 | Santelli, Jr. |
| 7,090,653 B2 | 8/2006 | Moeller |
| 7,128,724 B2 | 10/2006 | Marsh |
| 7,141,031 B2 | 11/2006 | Garth et al. |
| 7,198,610 B2 | 4/2007 | Ingimundarson et al. |
| D542,919 S | 5/2007 | Leatt |
| 7,258,677 B2 | 8/2007 | Rudy, Jr. et al. |
| D552,742 S | 10/2007 | Leatt |
| 7,291,121 B2 | 11/2007 | Rudy, Jr. et al. |
| 7,297,127 B2 | 11/2007 | Lee et al. |
| 7,311,686 B1 | 12/2007 | Iglesias et al. |
| 7,371,221 B1 | 5/2008 | Baker |
| 7,371,222 B2 | 5/2008 | Heinz et al. |
| 7,399,288 B2 | 7/2008 | Chao |
| 7,442,176 B2 | 10/2008 | Cojbasic |
| D609,815 S | 2/2010 | Patterson |
| 7,674,234 B2 | 3/2010 | Calco et al. |
| D616,555 S | 5/2010 | Thorgilsdottir et al. |

(56) References Cited

U.S. PATENT DOCUMENTS

| | | | |
|---|---|---|---|
| D616,996 S | 6/2010 | Thorgilsdottir et al. | |
| D616,997 S | 6/2010 | Thorgilsdottir et al. | |
| D617,907 S | 6/2010 | Waller | |
| 7,815,585 B2 | 10/2010 | Vollbrecht | |
| 7,846,117 B2 | 12/2010 | Leatt et al. | |
| D631,167 S | 1/2011 | Leatt et al. | |
| 7,878,995 B2 | 2/2011 | Harty | |
| 7,896,827 B2 | 3/2011 | Ingimundarson et al. | |
| 7,981,068 B2 * | 7/2011 | Thorgilsdottir | A61F 5/055 128/846 |
| D643,978 S | 8/2011 | Abajo Alonso et al. | |
| D644,331 S | 8/2011 | Sandhu | |
| D644,332 S | 8/2011 | Sandhu | |
| 7,992,261 B2 | 8/2011 | Hammerslag et al. | |
| D647,623 S | 10/2011 | Thorgilsdottir et al. | |
| D647,624 S | 10/2011 | Thorgilsdottir et al. | |
| 8,038,635 B2 | 10/2011 | Dellanno | |
| 8,038,636 B2 * | 10/2011 | Thorgilsdottir | A61F 5/055 128/846 |
| D659,842 S | 5/2012 | Donaldson et al. | |
| D662,597 S | 6/2012 | Chang | |
| 8,216,167 B2 | 7/2012 | Garth et al. | |
| D666,302 S | 8/2012 | Joseph | |
| 8,257,292 B2 | 9/2012 | Linares | |
| 8,545,423 B2 | 8/2013 | Patron | |
| D692,568 S | 10/2013 | Chiang et al. | |
| D693,014 S | 11/2013 | Chiang et al. | |
| 8,679,044 B2 | 3/2014 | Thorgilsdottir et al. | |
| 8,932,243 B2 * | 1/2015 | Calabrese | A61F 5/055 602/18 |
| 9,132,027 B2 | 9/2015 | Calco | |
| D767,825 S | 9/2016 | Georgeson et al. | |
| 2002/0138028 A1 | 9/2002 | Ru Dy, Jr. et al. | |
| 2002/0156408 A1 | 10/2002 | Cheatham | |
| 2002/0156409 A1 | 10/2002 | Lee et al. | |
| 2002/0169401 A1 | 11/2002 | Walpin | |
| 2002/0173737 A1 | 11/2002 | Miyaji et al. | |
| 2003/0055367 A1 | 3/2003 | Dominguez | |
| 2003/0060744 A1 | 3/2003 | Caille et al. | |
| 2003/0181838 A1 | 9/2003 | Garth | |
| 2004/0039318 A1 | 2/2004 | Santelli, Jr. | |
| 2005/0101896 A1 | 5/2005 | Calabrese | |
| 2007/0027418 A1 | 2/2007 | Calco et al. | |
| 2007/0073203 A1 | 3/2007 | Moenning et al. | |
| 2007/0270728 A1 | 11/2007 | Chao | |
| 2009/0247918 A1 | 10/2009 | Patron | |
| 2010/0137768 A1 | 6/2010 | Thorgilsdottir et al. | |
| 2010/0137769 A1 * | 6/2010 | Schulte | A61F 5/05875 602/22 |
| 2010/0268139 A1 | 10/2010 | Garth | |
| 2010/0298748 A1 | 11/2010 | Rosenfeld et al. | |
| 2011/0034844 A1 | 2/2011 | Thorgilsdottir et al. | |
| 2011/0066094 A1 | 3/2011 | Thorgilsdottir et al. | |
| 2011/0224591 A1 | 9/2011 | Thorgilsdottir et al. | |
| 2012/0053499 A1 | 3/2012 | Donaldson et al. | |
| 2012/0130295 A1 | 5/2012 | Haider | |
| 2012/0165712 A1 | 6/2012 | Calabrese | |
| 2013/0060179 A1 | 3/2013 | Modglin | |
| 2013/0281899 A1 | 10/2013 | Suarez et al. | |
| 2013/0281900 A1 | 10/2013 | Suarez et al. | |
| 2013/0310722 A1 | 11/2013 | Thorsteinsdottir et al. | |
| 2014/0012172 A1 | 1/2014 | Calco | |
| 2014/0107551 A1 | 4/2014 | Modglin | |
| 2014/0323938 A1 | 10/2014 | Suarez et al. | |
| 2015/0216708 A1 | 8/2015 | Garth et al. | |
| 2016/0287424 A1 | 10/2016 | Webster et al. | |
| 2017/0246022 A1 | 8/2017 | Calco et al. | |
| 2018/0078400 A1 | 3/2018 | Hsu et al. | |
| 2018/0078401 A1 | 3/2018 | Hsu et al. | |

FOREIGN PATENT DOCUMENTS

| | | |
|---|---|---|
| CN | 201150587 Y | 11/2008 |
| CN | 201602923 U | 10/2010 |
| CN | 102227196 A | 10/2011 |
| CN | 202015274 U | 10/2011 |
| DE | 19547115 A1 | 6/1997 |
| DE | 19849302 A1 | 4/2000 |
| DE | 100 57 286 A1 | 5/2002 |
| EP | 1738724 A1 | 1/2007 |
| EP | 2653139 A1 | 10/2013 |
| EP | 2886088 A1 | 6/2015 |
| FR | 2 814 362 A1 | 3/2002 |
| GB | 2 165 157 A | 4/1986 |
| GB | 2 453 996 A | 4/2009 |
| JP | 2007-330808 A | 12/2007 |
| WO | 94/09728 A1 | 5/1994 |
| WO | 95/22304 A1 | 8/1995 |
| WO | 96/40018 A1 | 12/1996 |
| WO | 9843568 A1 | 10/1998 |
| WO | 2014102340 A1 | 7/2014 |

OTHER PUBLICATIONS

Product Brochure, "Capital Collar Enhanced," DeRoyal, 2014, 2 Pages.

Product Brochure, "Instructions for Use Eclipse Cervical Collar," VQ OrthoCare, 2015, 2 Pages.

Product Brochure, "Miami J Advanced by OSSUR," www.ossur.com, 2012, 4 Pages.

Product Brochure, "Miami J Cervical Collar," www.ossur.com, 1 Page.

Product Brochure, "Proglide Cervical Collar," OPTEC, www.optecusa.com, 1 Page.

Product Brochure, "Vista Upper Spine," Aspen Medical Products, 2015, 6 Pages.

Tescher et al., "Range-of-Motion Restriction and Craniofacial Tissue-Interface Pressure From Four Cervical Dollars", The Journal of Trauma Injury, Infection, and Critical Care, vol. 63, No. 5, Nov. 2007, pp. 1120-1126.

"Ossur Is Immobilization", www.ossur.com, 2008, pp. 1-16.

"Miami J Patient Care Handbook", www.ossur.com, 2010, pp. 1-16.

Jacobson et al. "Improving Practice Efforts to Reduce Occipital Pressure Ulcers", Journal of Nursing Care Quality, vol. 23, No. 3, 2008, pp. 283-288.

Bell et al. "Assessing Range of Motion to Evaluate the Adverse Effects of Ill-Fitting Cervical Orthoses", The Spine Journal, vol. 9, 2009, pp. 225-231.

Karason et al. "Evaluation of Clinical Efficacy and Safety of Cervical Trauma Collars: Differences in Immobilization, Effect on Jugular Venous Pressure and Patient Comfort", Scandinavian Journal of Trauma, Resuscitation and Emergency Medicine, 2014, pp. 1-7.

Chinese Search Report from CN Application Serial No. 200980147713.8, dated Dec. 6, 2012.

European Search Report from EP Application Serial No. 13165274.5, dated Jul. 17, 2013.

International Search Report from PCT/US2009/006335, dated Mar. 11, 2010, 3 pages.

Written Opinion of the International Searching Authority from PCT/US2009/006335, dated Mar. 11, 2010, 5 pages.

International Search Report from corresponding PCT Application No. PCT/US2013/041586, dated Oct. 1, 2013.

International Search Report and Written Opinion from in PCT/US2010/002199, Dec. 27, 2010, 9 pages.

Levangie et al., "Joint Structure and Function: A Comprehensive Analysis", Fourth Edition,Chapter 4: The Vertebral Column, 2005 F.A. Davis Company, Philadelphia, PA, pp. 161-164.

Hsu et al., AAOS Atlas of Orthoses and Assistive Devices, Mosby, Elsevier Fourth Edition, 2008, Philadelphia, PA, p. 117-122.

Product Information Sheet, Philadelphia Tracheotomy Collar, obtained from www.ossur.com, prior to Aug. 6, 2010, 1 page.

Product Information Sheet, Plastazote Sheets, WBC Industries, obtained from www.wbcindustries.com prior to Aug. 5, 2010, 2 pages.

(56) References Cited

OTHER PUBLICATIONS

International Search Report from PCT Application No. PCT/US2016/026222, dated Jun. 14, 2016.

* cited by examiner

CERVICAL COLLAR

FIELD OF THE INVENTION

The invention relates generally to the field of orthopedic or prosthetic devices and more specifically to cervical collars having height and circumferential adjustment with a mandible support.

BACKGROUND

Cervical collars are used in the treatment, stabilization, immobilization, and therapy of cervical trauma. Some collars are intended to provide support for whiplash and other such injuries where support for the head and neck is needed. Other collars are intended for near complete immobilization of the head and neck, such as in an EMS pre-hospital setting.

There is often a rush to apply these collars onto the wearer due to the acute nature of cervical injuries. The collar must be selected to accommodate the wearer's size in a quick manner for effective stabilization and immobilization of the neck of the wearer.

Known cervical collars restrict spine flexion, extension and rotation to promote wearer recovery. Such known collars also include a trachea opening allowing healthcare clinicians to perform quick carotid pulse monitoring and emergency tracheotomies while providing cervical immobilization.

A drawback to known collars is that they are individually sized for a variety of standard wearer sizes. There is a need to store many different sized collars in inventory which significantly adds to the cost for using such collars. If there is an emergency, and the proper sized collar is not available, the caregiver is given little option other than to apply a poorly fitting collar on the wearer since many known collars provide minimal size adjustment.

Proper sizing is critical for wearer immobilization and comfort. While there are a variety of different standard sizes, the wearer may have dimensions which fall outside of the standard sizes, and wear a poorly fitting collar that insufficiently immobilizes the wearer's neck. Such poor fitting may also cause significant discomfort to the wearer.

Over time, swelling of the wearer's neck may reduce which further complicates the sizing of the collar. This may lead to the need for disposing the initially selected collar and replacing it with a new collar. This may lead to waste and an increase in cost.

When sizing a cervical collar, the first notable dimension concerns the height. The height is measured by the vertical distance from the tip of the chin to the sternum; the other key dimension concerns the circumference of the wearer's neck.

Besides sizing, proper application of the collar is necessary for immobilization and wearer comfort. A typical collar includes of front and rear components packaged as a set according to the size of the wearer.

When applying a collar to the wearer, the rear component of the collar applies to the back of the wearer's neck. Once the back wearer is positioned appropriately, the front component of the collar is positioned against the front or anterior portion of the neck so a chin support is placed against the chin. The front component is centered to secure neutral alignment. The front component overlaps the rear component to ensure effective immobilization and comfort. Straps are then tightened to the collar with a bilateral adjustment which secures the wearer's cervical region in neutral alignment.

An issue with known collars is that the collars typically only provide support under the mid-front of the chin, and lack support under the mandible (lower jaw or jaw bone). From this, there is often undue pressure exerted on the chin of the wearer, which may cause discomfort and sores.

Another issue with known collars having frontal or anterior sternum footplates is that the footplate has a tendency to be positioned closer to the neck than the chin part of the collar, the footplate is too flexible, and the collar can be easily yet detrimentally fitted too tight resulting in the sternum pad to sit on a clavicle.

Yet another issue with known collars is that such collars with an adjustable sternum footplate is that existing locking system were insufficiently strong to prevent buttons or locks from unlocking.

SUMMARY

The present disclosure describes a cervical collar having height and circumferential adjustment to accommodate a wide variety of sizes of different patients and to accommodate size changes caused by increased or decreased swelling of the affected anatomical portions of the patients.

Features of the cervical collar include a removable height support piece to allow the collar to be adjusted or removed for cleaning or to check for pressure sores, without removing life support attachments such as breathing and feeding tubes. The support piece includes a footplate without a hinge at its extension to provide a more rigid footplate when applied against a wearer's sternum so a chin insert for supporting the mandible is generally aligned or closely aligned with one another.

A locking system is provided for locking the support piece in that the locking system includes spring locks for securely retaining the support piece to the anterior component. The support piece is stiffened to assure that the support piece provides stable and secure support.

Flexible or compliant edges and anatomically shaped portions on the cervical collar are provided to accommodate different sized users, to accommodate changes in anatomical shape due to an increase or decrease in swelling, and to prevent pressure peaks, even if the collar is improperly applied to the patient.

The disclosed cervical collar is configured to conform to the anatomy of the patient, and to further to be a generally constant contact collar that contacts the skin of the patient such that when the collar allows some amount of patient movement, the collar moves with the patient.

The combination of flexible or compliant edges and anatomically shaped portions on the cervical collar with ventilation mechanisms, such as ventilation slots, allow the collar to have intimate contact with the skin of the patient (with or without a liner). The posterior component is provided with a plurality of living hinges formed by constructing a flexible posterior of the posterior component in combination with a main support piece, particularly along a plurality of slots formed alongside portions of the posterior component. The flexible material forming the flexible edge extends from the periphery of the posterior component to the slots, at least on one side of the posterior component, which are provided for allowing a strap to secure to the posterior component.

The cervical collar has a mandible support that distributes pressure more evenly about the chin and mandible to prevent excessive pressure. The collar's attachment system of anterior and posterior components is adjustable to provide a more flexible strap system under the mandible portion of the collar.

BRIEF DESCRIPTION OF THE DRAWINGS

These and other features, aspects, and advantages of the present invention will become better understood regarding the following description, appended claims, and accompanying drawings.

Figure 1A:
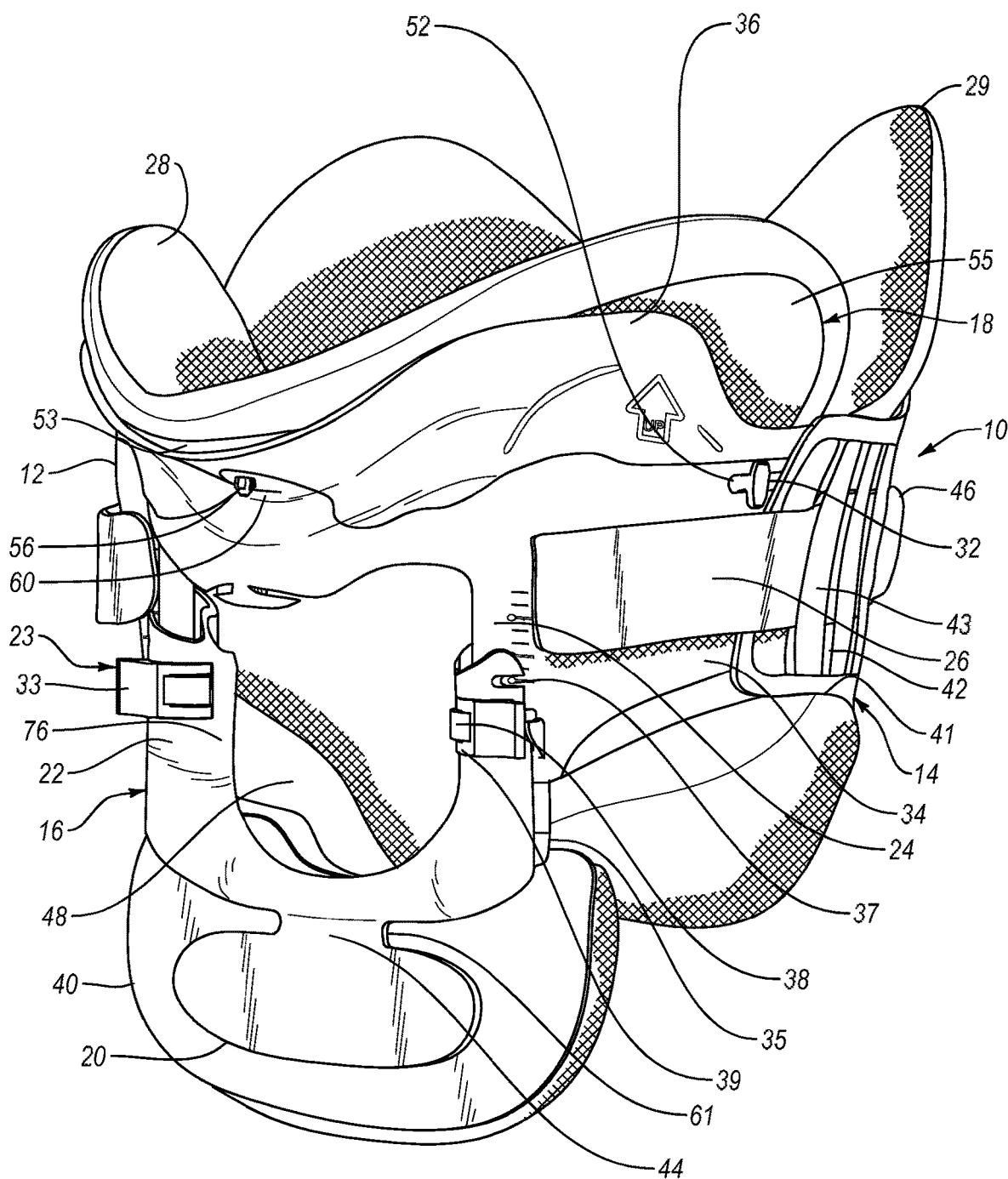
FIG. 1A is a perspective view of an embodiment of a cervical collar according to the present disclosure.

The drawing figures are not necessarily drawn to scale, but instead are drawn to provide a better understanding of the components thereof, and are not intended to be limiting in scope, but rather to provide exemplary illustrations. It should further be noted that the figures illustrate exemplary configurations of a cervical collar having height and circumferential adjustment and the respective components thereof, and in no way limit the structures or configurations of a cervical collar and components thereof according to the present disclosure.

DETAILED DESCRIPTION OF VARIOUS EMBODIMENTS

A. Environment and Context

Embodiments of an orthopedic device are provided for stabilizing and supporting anatomical portions of a patient, for example, the neck and head of a patient.

Although the embodiments of the disclosure are adapted for supporting and stabilizing anatomical portions of many patients having various anatomical shapes and sizes, the embodiments of the disclosure may also be dimensioned to accommodate different types, shapes and sizes of anatomical portions.

Exemplary materials and configurations for components of the orthopedic device, such as the structural supports or shells and flexible or compliant portions, and exemplary uses and connection mechanisms are described in U.S. Pat. No. 5,180,361, granted January 1993, U.S. Pat. No. 5,445,602, granted August 1995, U.S. Pat. No. 5,622,529, granted April 1997, U.S. Pat. No. 5,632,722, granted May 1997, U.S. Pat. No. 5,716,335, granted February 1998, U.S. Pat. No. 6,071,255, granted June 2000, U.S. Pat. No. 6,254,560, granted July 2001, U.S. Pat. No. 6,663,581, granted December 2003, U.S. Pat. No. 7,018,351, granted March 2006, U.S. Pat. No. 7,198,610, granted April 2007, and U.S. Pat. No. 7,981,068, granted Jul. 19, 2011, and U.S. patent application publication 2011/0066094, published Mar. 17, 2011, and all incorporated in the entirety by reference.

For ease of understanding the disclosed embodiments of an orthopedic device, the anterior and posterior portions of the orthopedic device are described independently. The anterior and posterior portions of the orthopedic device function together to form a supporting and stabilizing collar that encompasses the anatomical portions of the wearer.

For further ease of understanding the embodiments of an orthopedic device as disclosed, a description of a few terms is necessary. As used, the term "proximal" has its ordinary meaning and refers to a location situated next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. The term "anterior" has its ordinary meaning and refers to a location ahead of or to the front of another location.

The terms "rigid," "flexible," "compliant," and "resilient" may be used to distinguish characteristics of portions of certain features of the orthopedic device. The term "rigid" should denote that an element of the device is generally devoid of flexibility. Within the context of support members or shells that are "rigid," it is intended to indicate that they do not lose their overall shape when force is applied, and in fact they may break if bent with sufficient force. The term "flexible" should denote that features are capable of repeated bending such that the features may be bent into retained shapes or the features do not retain a general shape, but continuously deform when force is applied.

The term "compliant" may qualify such flexible features as generally conforming to the shape of another object when placed in contact therewith, via any suitable natural or applied forces, such as gravitational forces, or forces applied by external strap mechanisms. The term "resilient" is used to qualify such flexible features as generally returning to an initial general shape without permanent deformation. As for the term "semi-rigid," this term is used to connote properties of support members or shells that provide support and are free-standing; however such support members or shells may have some degree of flexibility or resiliency.

B. Embodiments of the Cervical Collar

Under the embodiments described, the cervical collar 10 includes an anterior component 12 and a posterior component 14, which are similar in part to those described in U.S. Pat. No. 7,981,068. The cervical collar 10 also includes a height support 16 adjustably securing to the anterior component 12 and combining therewith to form a tracheal open access area 48. A two part liner 28, 29 can be provided as an interface between the patient and the respective anterior and posterior components 12, 14. A removable chin support 18 is secured to an interior or inside portion of the anterior support 12. A strapping system 26 is provided to secure the anterior and posterior components 12, 14 to one another.

Both the anterior and posterior components 12, 14 may be formed at least from a rigid or semi-rigid main support portion 34 and a resilient or flexible portion 36 surrounding sections of the main support portion 34. A fuller explanation of these components and variations are found in U.S. Pat. No. 7,981,068.

The adjustable height support 16 includes two upright legs 22 configured to cooperate with depending projections 24 formed by the anterior component 12. Recessed portions are formed in the upright legs 22 and have a corresponding shape to the depending projections 24 for receiving the respective depending projections 16 to allow the adjustable height support 16 to be positioned at different heights along the depending projections 24. A more detailed description of the height support is found in U.S. patent application publication 2011/0066094.

Figure 1B:
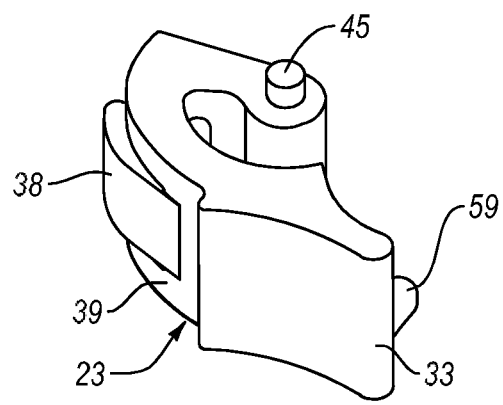
FIGS. 1B and 1C are respectively a side perspective view and a rear perspective view of the locking button of the height support of FIG. 1A.
Figure 1C:
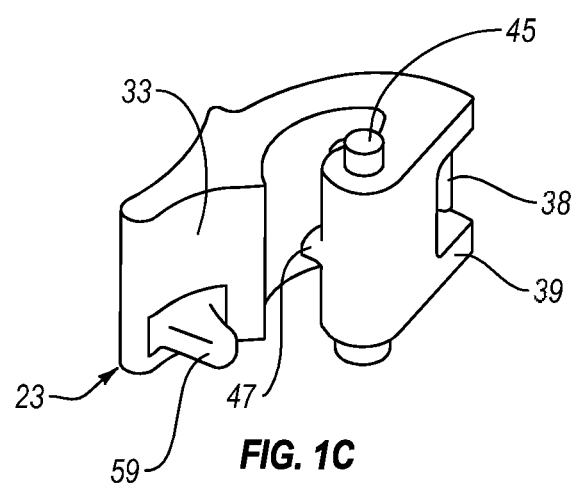

As shown in FIGS. 1B and 1C, each upright leg 22 includes a locking button 23 that can be manipulated to selectively lock the adjustable height support 16 from being adjusted to a shorter height. The buttons 23 are received in appropriately sized and shaped cut out portions of the upright legs 22

Each button 23 includes a pivot axle 45 (not shown but resembling an axle in U.S. patent application publication 2011/0066094), received in the upright leg 22, to allow the button 23 to pivot thereon from an engaged, locked position, to a disengaged, unlocked position. The button 23 may include at least one locking protrusion configured to selectively engage a corresponding portion of the cut out portions of the upright legs 22 to selectively lock the button 23 in the engaged, locked position to prevent accidental movement of the height support 16 to a shorter height.

Figure 1D:
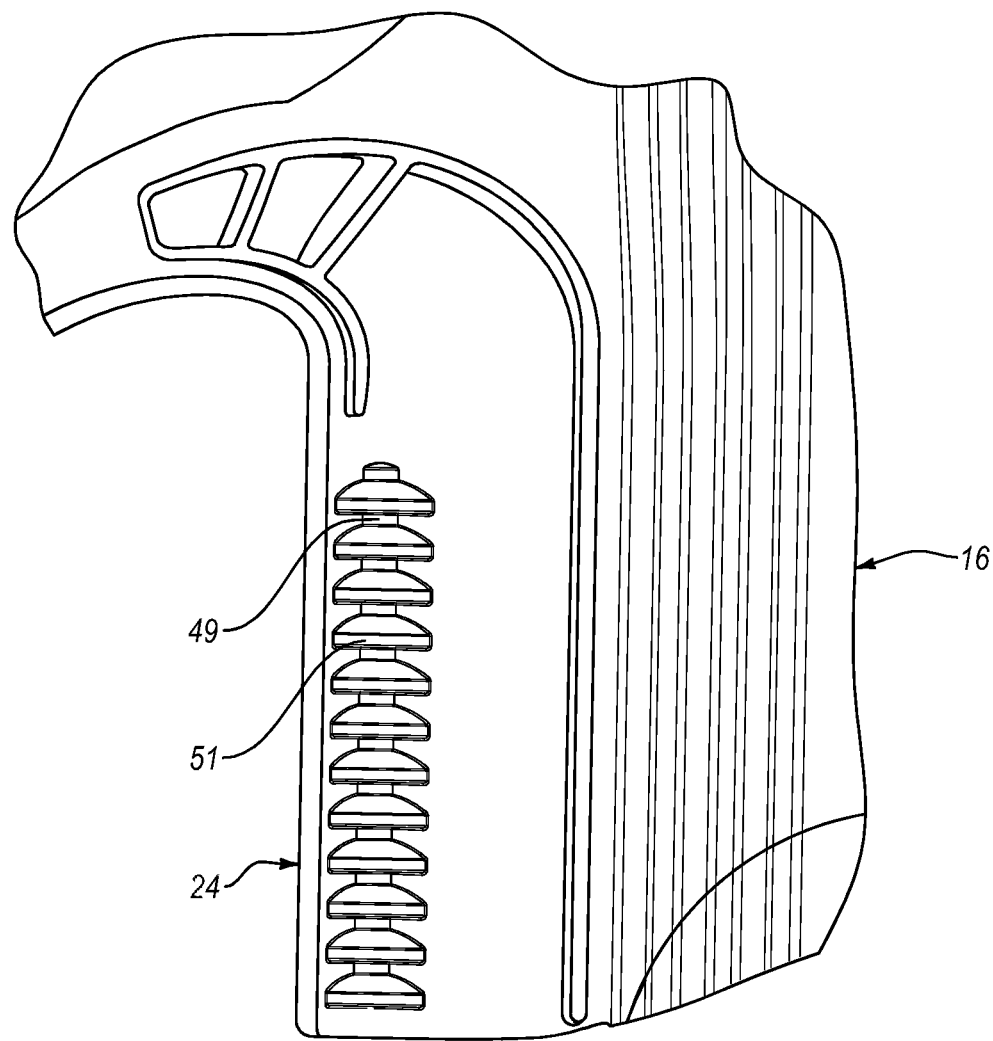
FIG. 1D is a rear schematic view of an interior surface of the depending projection of the anterior component.

A tooth or teeth 47 (shown with a tooth) may be formed along a reduced thickness portion of the pivot axle 45 for selective engagement with the locking projections or ratchets 51 formed on the depending projections 24, as shown in FIG. 1D. The locking projections 51 are preferably flat surfaces and each have a height spaced apart by slots 49 along the height of the depending projections 24. The teeth 47 may be formed similarly, but in opposition to, the locking projections 51, such that the teeth include a first edge having a first thickness that tapers out to a linear edge having a second thickness that is larger than the first thickness, wherein the linear edges of the teeth engage with the linear edges of the locking projections or ratchets to selectively lock the height support from being adjusted to a shorter height.

A protrusion 59 may extend from the lever 33 and engage an opening formed along the upright leg 22, or alternatively abut against a side of the upright leg.

When the buttons 23 are pivoted to the disengaged, unlocked position, the teeth are removed from contacting the locking projections 51 formed on the depending projections 24. The height support 16 can freely move either up or down to either decrease or increase the height. In this manner, the position of the height support 16 on the associated depending projections 24 can be altered to accommodate different anatomical sizes of wearers.

When the buttons 23 are pivoted to the engaged, locked position, the teeth are in contact with the locking projections or ratchets formed on the depending projections, and the engagement of the linear edges of the teeth and the locking projections or ratchets prevents the movement of the height support 16 in the upward direction to prevent the height support 16 from being adjusted to a shorter height. However, since the teeth are formed on a reduced thickness portion of the pivot axle, the height support can be moved downward to be adjusted to an increased height, since the reduced thickness portion of the pivot axle provides resiliency to the teeth and allows the tapered portions of the teeth to slide over the tapered portions of the locking projections or ratchets.

In this manner, the position of the height support 16 on the associated depending projections can be adjusted to increase the height without manipulating the buttons 23. This feature is a benefit for quickly applying the cervical collar to a patient. The cervical collar can be packaged with the height support 16 positioned in the shortest height configuration, to save on packaging space, and the buttons 23 positioned in the engaged, locked position.

Fine tuning of the height of the cervical collar can be achieved by unlocking and pivoting the buttons 23 to the disengaged, unlocked position, and adjusting the height of the height support 16 as needed.

Height adjustment indicia may be provided on the depending projections to provide easy sizing of the cervical collar using predetermined sizes, such as small, medium, large, etc. The height adjustment indicia can be in standardized, color coded markings and/or lines that reflect standardized marking systems used to indicate patient sizes. Other indicia, such as alphanumeric labels, can also be used. The height adjustment indicia cooperate with leading edges of the adjustable height support to provide an indication of the current sizing of the cervical collar.

According to the embodiment of FIG. 1, the buttons 23 include a resilient tab 38 that engages a side portion 76 of the upright leg 22 to secure placement of the leg 22 relative to the depending projections 24. A lever 33 is formed on an opposite side to the resilient tab 38 to facilitate closing of the button 23. The tab 38 may be resiliently biased to extend over the side portion 76, whereas adjacent arms 39 to the tab 38 do not extend over the side portion 76, and may fit within the cut out portion defined by the legs 22 that permit rotation of the buttons about the axle. The tab 38 may be disengaged by being pressed into the cut out portion to rotate the button and disengage from the depending projections 24.

The tab has the advantage in that it prevents the size of the collar, particularly the height support, from being adjusted accidentally; it securely retains the collar. The tab requires the button to be pushed down prior to unlocking the button, firmly retaining the button against accidental adjustment, as shown with FIGS. 8A-8D. A retainer 35 is formed on the anterior component adjacent to the height support 16 to guide sliding motion of the height support 16 relative to the anterior component.

A non-hinged distal sternal part 20 is connected at connection 44 to the distal end of the adjustable height support 16, and includes a footpad 40 thereon. Unlike in prior art cervical collars, the connection 44 is preferably provided without a hinge to reduce pressure points on the sternum which occurs when a hinge is provided as the connection. The thickness at the connection 44 is continuous without variations; a living hinge would be considered to have a variable thickness to facilitate a bending by forming a weakened section.

By removing a hinge at the connection 44, the chin support 18 and the sternum part 20 are more in line with each other to avoid the footpad 40 from being placed too close to the neck than the chin support itself which should overlie the sternum plate to better distribute pressure by the footpad 40. The removal of the hinge at the connection makes the connection more rigid, and prevents the collar from being fitted too tight and the footpad being placed on the clavicle rather than the sternum.

The footpad 40 can be an integrally formed footpad, or a removable and/or replaceable footpad configured to engage an anatomical portion, such as the sternum. To provide comfort to the wearer and to avoid skin ulceration, the footpad 40 can be a resilient or a compliant pad formed by overmolding. The footpad 40 can also be formed as open or closed cell foam padding, and/or a disposable hydrophilic foam pad.

Figure 2:
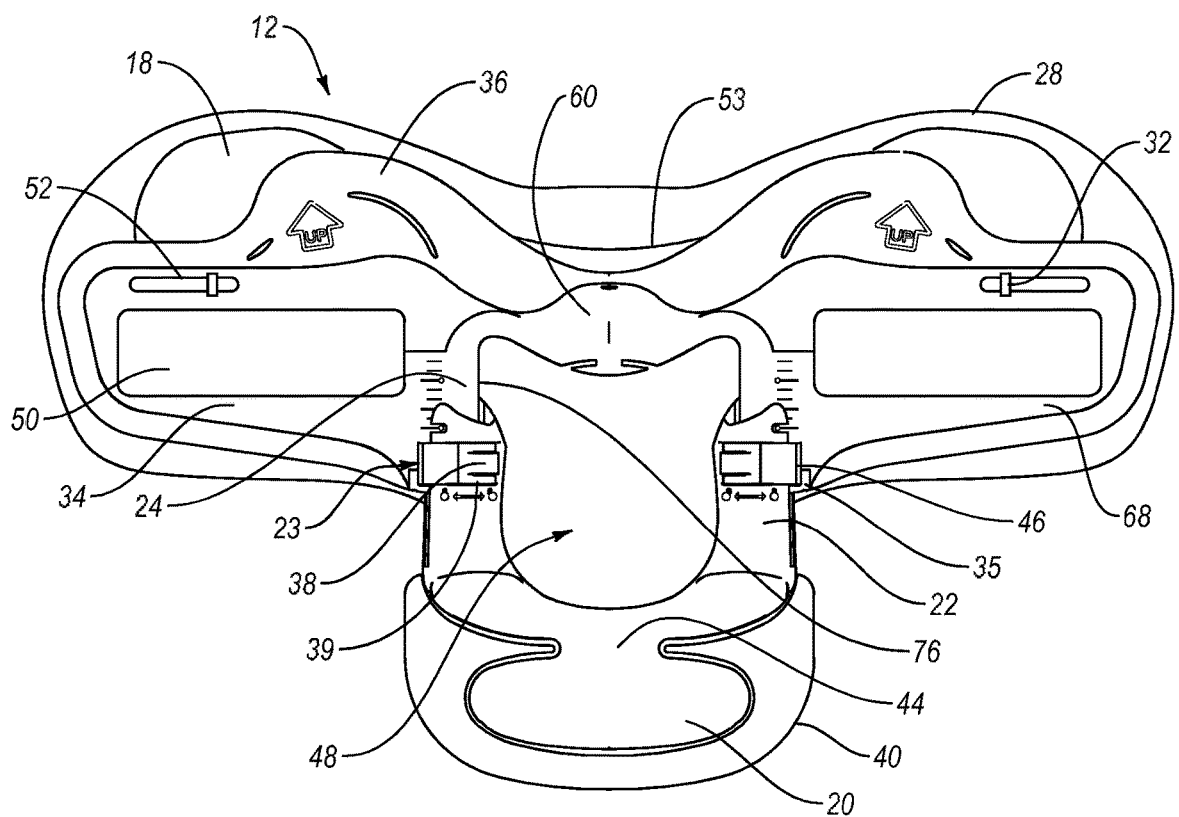
FIG. 2 is a front view of an anterior component of the cervical collar according to FIG. 1.
Figure 3:
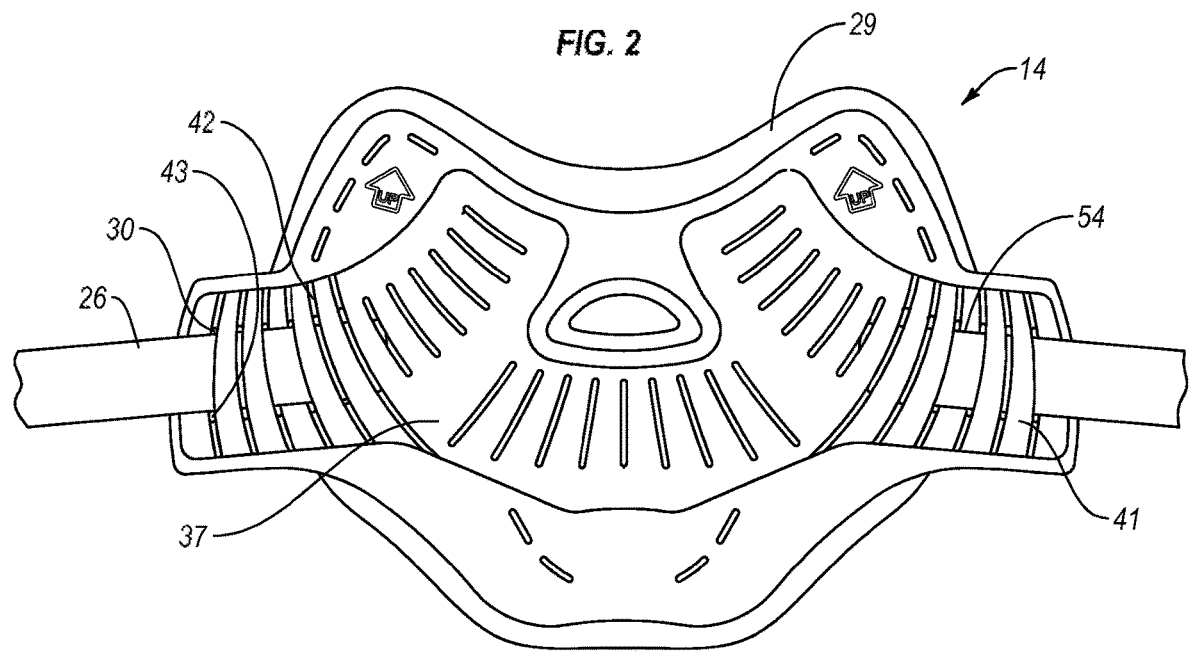
FIG. 3 is a front view of a posterior component of the cervical collar according to FIG. 1.

As best seen in FIGS. 1-3, the posterior component 14 has side extensions 41 that include a plurality of spaced substantially vertically oriented or angled arcuate slots 30 that aid with ventilation of the orthopedic device in use, and provide affixation regions 46 by which the straps 26 of the strapping system may be looped with loop 54, secured, threaded and applied to the receiving section 50 on the anterior component.

To provide additional resiliency or living hinges, flexible material regions 42 are provided at opposed ends of the slots 30 to allow the posterior component 14 to bend circumferentially at the side extensions 41 to conform to the anatomical portion of the user, such as the neck. Side portions 43 bordering the slots are preferably formed from a more rigid material to withstand forces exerted by the strap 26 which may be selectively looped 54 at one end to at least one of the side portions 43. The flexible material regions 42 may cover thinned regions of the rigid material or the side portions 43 may be embedded within the flexible material forming at least part of the flexible material regions 42.

The strapping system has an advantage of preventing unexpected opening of the collar or separation of the anterior component from the posterior component. The slots provide vents and selective points for threading and securing the strap. The flexible material regions also allow the posterior component to better conform to the anatomy of the wearer which prevents the collar from opening up since the rigid material in combination with the flexible material now has breaks rather than urging the collar into an open configuration.

According to the embodiment of FIG. 1, the chin support 18 is centrally fixed at a center portion 53 secured to the anterior component 12 at a supporting spring portion 60 by a locking pin 56 extending from the chin support 18. The spring portion 60 provides a stable but dampening support under the chin of the patient, and restricts flexion. Using the supporting spring portion 60 in combination with a flexible edge of the flexible portion also aids with reducing or eliminating pressure points.

Side or mandible portions 55 of the chin support 18 slidably engage slots 52 formed from the rigid or semi-rigid main support portion 34 and are located alongside corresponding side extensions 68 of the anterior support 12. The side portions 55 may also pivot generally upwardly and downwardly relative to the side extensions due to the connection therewith. The side portions 55 have a retention element 32 retained by the slots 52 which permit the side portions 55 to move relative to the anterior support 12 to conform to movement and anatomy of a wearer's chin.

Figure 4:
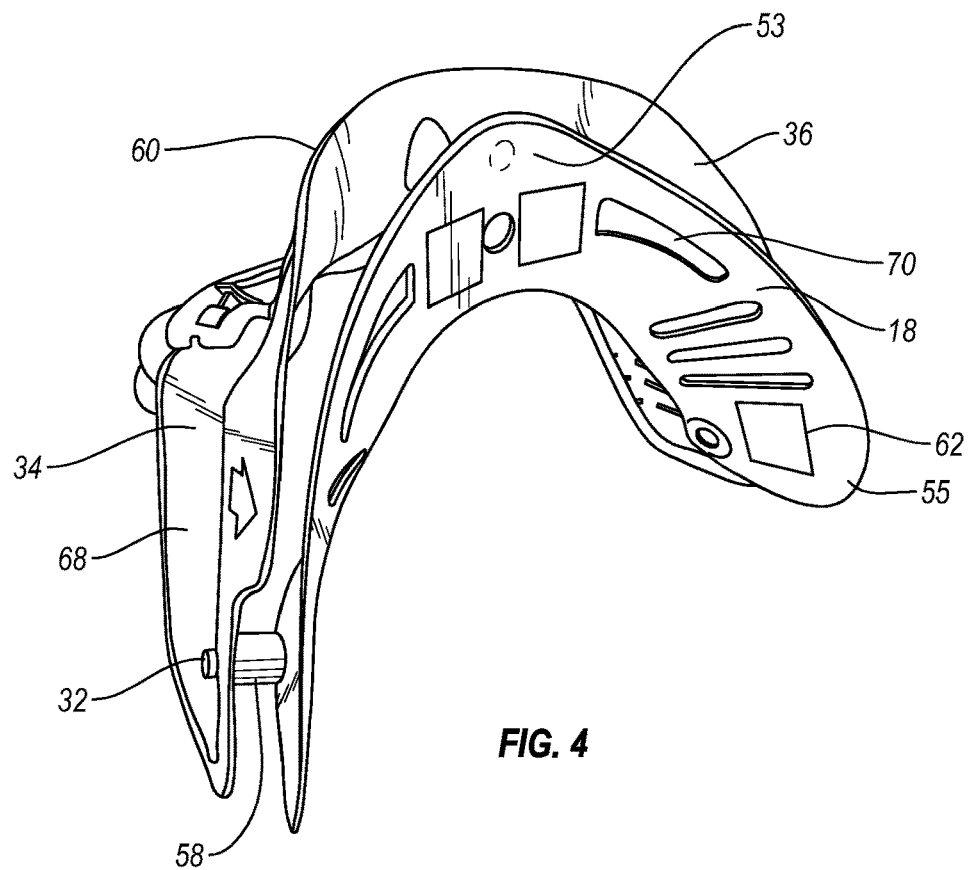
FIG. 4 is a perspective detail view showing of a chin support embodiment on the anterior component of FIG. 1.

In referring to the embodiment of FIG. 4, while the center portion 53 is secured against the spring portion 60 (depicted as spaced away since the locking pin 56 has not yet been pressed to engage the spring portion), the chin support 18 includes spacers 58 on the side portions 55 at which the retention elements 32 extend. The side portions 55 are used to space the chin support 18 away from the side extensions 68 to provide better support under the wearer's mandibles.

The chin support 18 may include appropriate hook and loop elements 62, and may define a plurality of ventilation features 70. The liner 28 may extend over the chin support continuously with the rest or portions of the anterior component 12.

Figure 5:
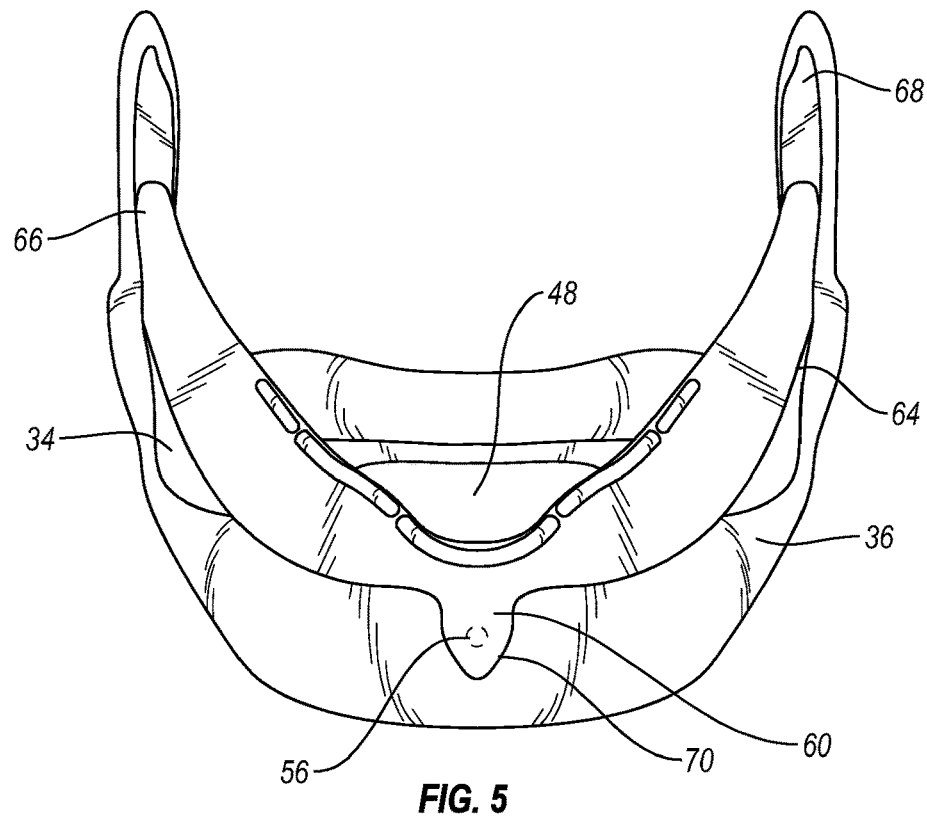
FIG. 5 is a top view showing another chin support embodiment on the anterior component of FIG. 1.
Figure 6:
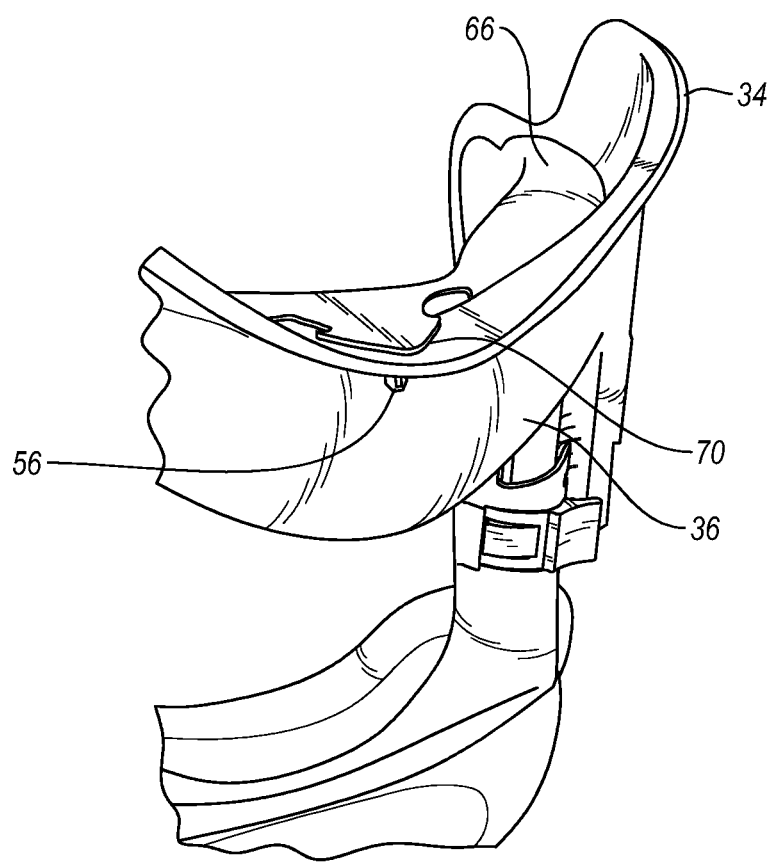
FIG. 6 is a perspective detail view showing the chin support of FIG. 5 on the anterior component of FIG. 1.

In observing FIGS. 4-6, each of the chin supports 18, 64 depicted have a different contour at the center portion 53, 70 which may be adapted for different anatomies of wearers. In the chin support 18 of FIG. 4, the center portion is generally continuously formed with the side portions 55 to provide a greater surface area for the chin and mandibles. In the variation of FIGS. 5 and 6, the chin support 64 has a narrowed center portion 70 which has a shape generally corresponding to the spring portion 60, and extends more outwardly inwardly toward the wearer's mandible at side portions 66. There are no spacers to this variation unlike in the variation of the chin support 18 of FIGS. 1-4.

Figure 7:
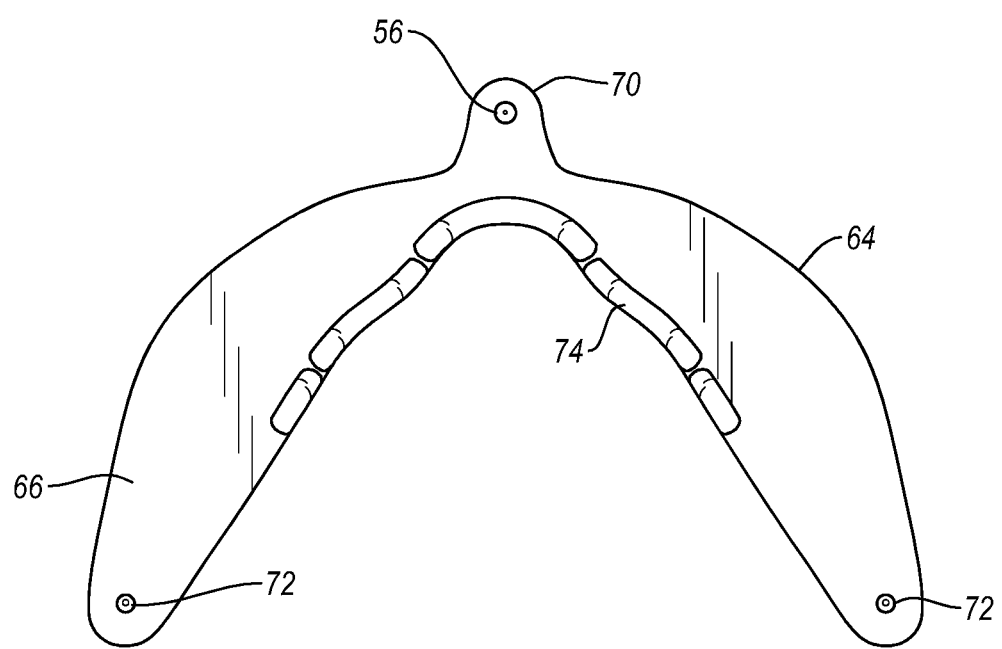
FIG. 7 is a top plan view showing the chin support embodiment of FIG. 5.

The chin support 64 of FIGS. 5 and 6 may retrofit existing cervical collars, as shown by the example of FIG. 7. The chin support 64 has a central locking pin 56 at the center portion and side pins 72 which may be inserted and locked to corresponding apertures that can be formed through existing collars. The chin support 64 may be provided with appropriate spacer protrusions 74 formed along its periphery as considered necessary to better place the chin support 64 against the wearer.

The chin support eliminates pressure points on the chin and mandible of the wearer by providing a larger surface and extended support, such as by the spacers, which enable the chin support to closely conform to the chin and the mandible. The sliding mechanism or connection of the chin support to the anterior component enables the chin support to closely conform to various anatomies and to accommodate swelling as the wearer undergoes treatment and heals.

Figure 8A:
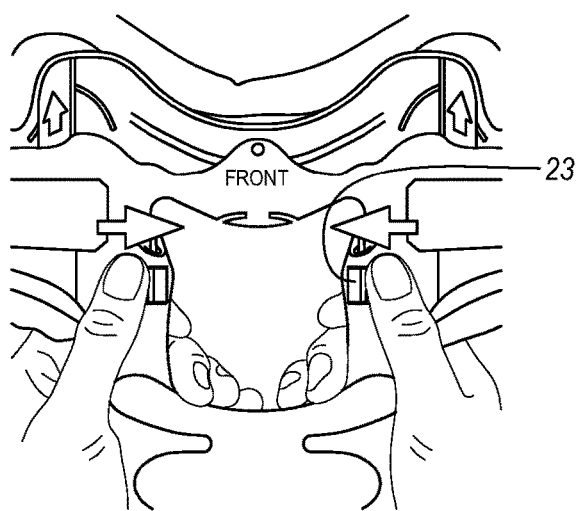
FIGS. 8A-8D show various steps of adjusting the height support.
Figure 8B:
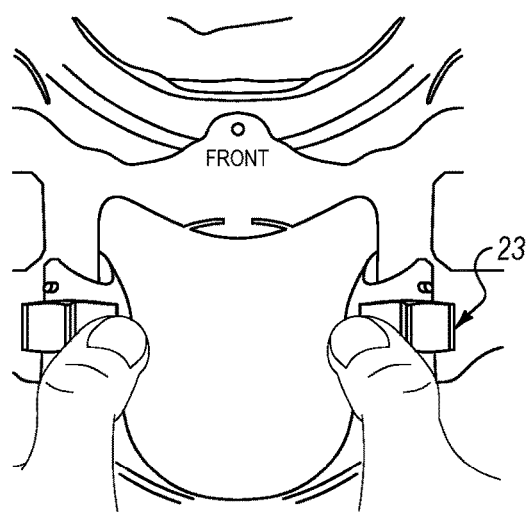
Figure 8C:
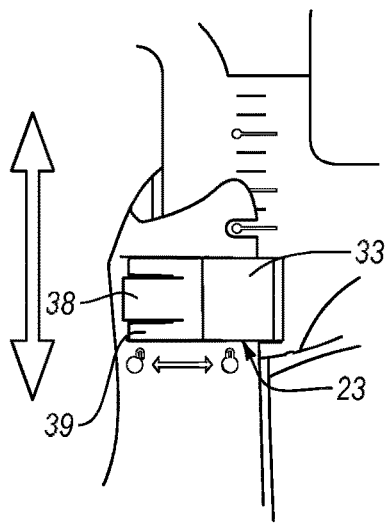
Figure 8D:
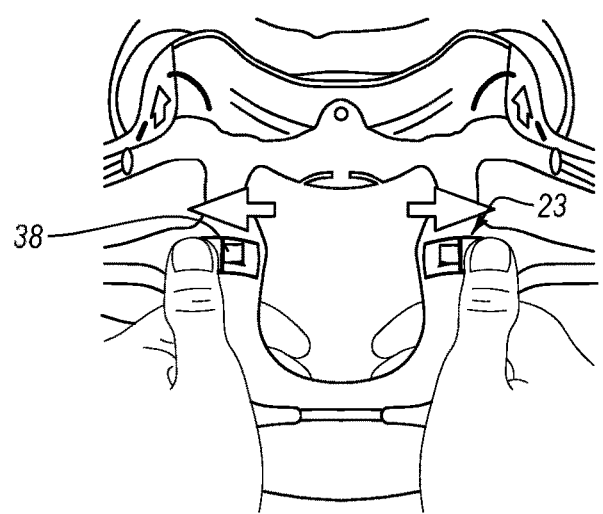

In observing FIGS. 8A-8D and the foregoing drawings, various steps may be employed for sizing the collar. First, FIG. 8A shows that the locking buttons are unlocked by squeezing them together. If the locking buttons are already locked, the tab is pressed and released, as shown in FIG. 8B. FIG. 8C shows that once the wearer's phenotype is determined, preferably from a sizing chart, the height support is adjusted to the appropriate height setting according to the indicia on the legs. In FIG. 1, a cut-away 37 is used to identify one of several different sizes that may be listed on the depending projections 24. Once the sizing is set, the locking buttons are locked by being rotated outward or away from the midline of the collar. Tamper resistance is obtained by ensuring the locking buttons are rotated outward until an audible click is heard by the tab placed into engagement with the side portion of the leg.

Figure 9A:
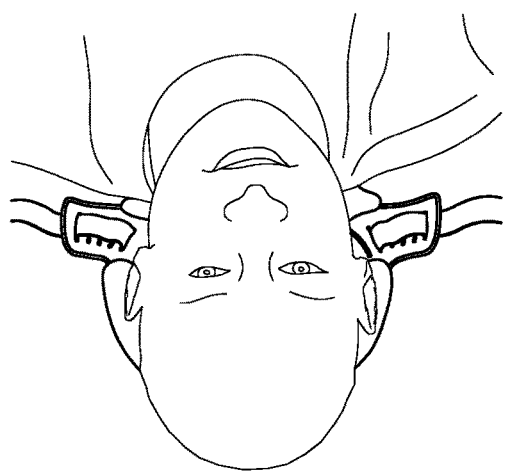
FIGS. 9A-9F show various steps of donning the cervical collar.
Figure 9B:
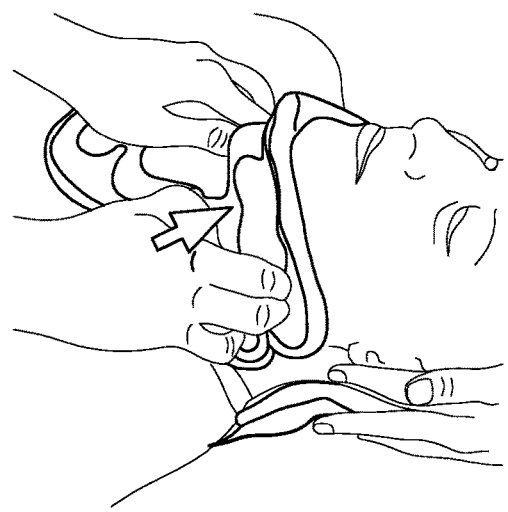

FIGS. 9A-9F exemplify application of the collar. According to FIG. 9A, the wearer is positioned with arms to the side, shoulder down and head centrally aligned. The posterior component is slid behind the wearer's neck and is centered thereagainst. In FIG. 9B, the anterior component (having already been presized) is placed up under the chin in which the front edge of the chin support is lined up with the front of the wearer's chin. The sides of the collar front should be oriented up, off the trapezius and toward the ears.

Figure 9C:
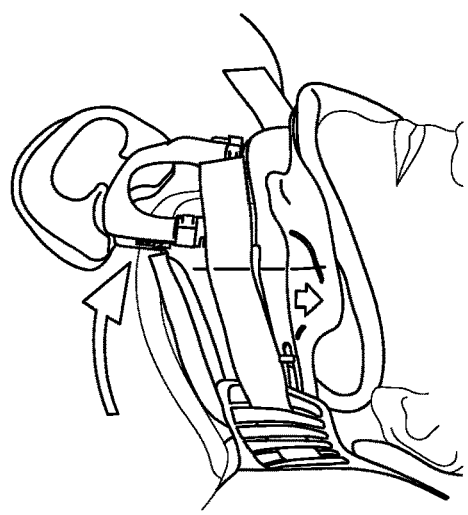

In reference to FIG. 9C, while holding the anterior component securely, the ends of the collar, including the footpad, are curled snugly against the wearer's neck. The strap system is used to secure the anterior component to the posterior component in which the straps are attached to the anterior component from the posterior component one at a time, to an equal length on both sides. According to FIG. 9E, the straps are trimmed once the collar is secured on the wearer, and FIG. 9F shows the collar is marked to indicate where the straps should be located once the collar is removed.

Figure 9D:
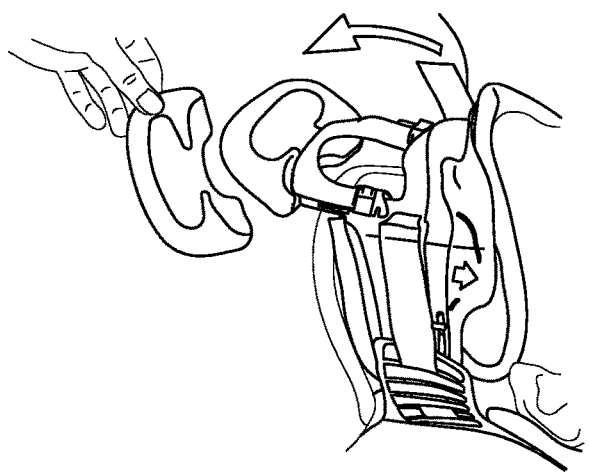
Figure 9E:
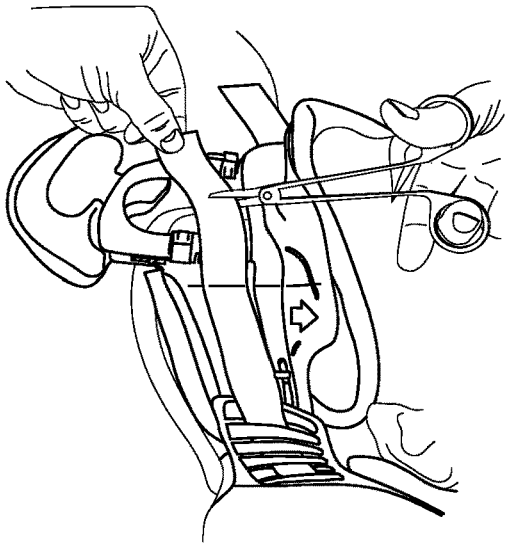
Figure 9F:
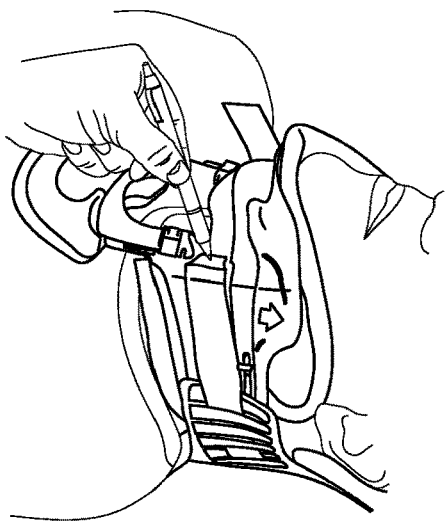

FIG. 9D depicts the instance where wearers of the collar remain in a supine position for an extended period of time consider removing a sternal pad belonging to the footplate for greater comfort. In this embodiment there are two pads attached to the footplate including a sternal pad and a primary pad adjacent the footplate structure itself, preferably made from SORBATEX which allows body moisture to pass through, dries quickly, inhibits microbial growth, and has good thermal conductivity. The primary pad should remain on the footplate.

Figure 10A:
FIGS. 10A-10B show various steps for removing the cervical collar.
Figure 10B:
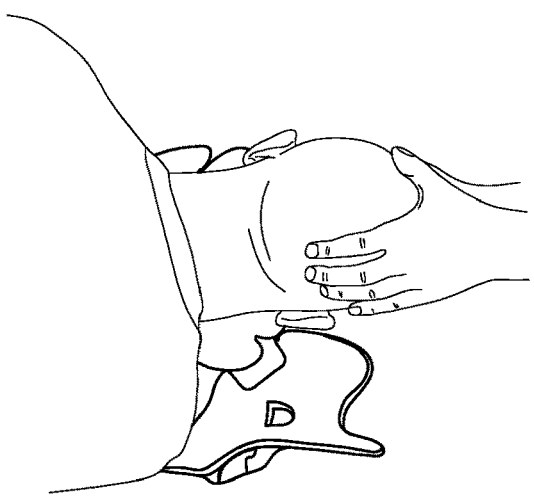

Turning to FIGS. 10A-10C, the collar may be removed from the wearer as follows. The wearer should be placed in a supine position with the bed flat, and with the arms to the side, shoulders down and the head centrally aligned. FIG. 10A shows that one of the straps is removed and the collar is hinged open. The wearer can be observed for healing, rashes or debris, or the collar can be completely removed. FIG. 10B shows how the straps may be removed, with the anterior and posterior components separated from one another.

Figure 11:
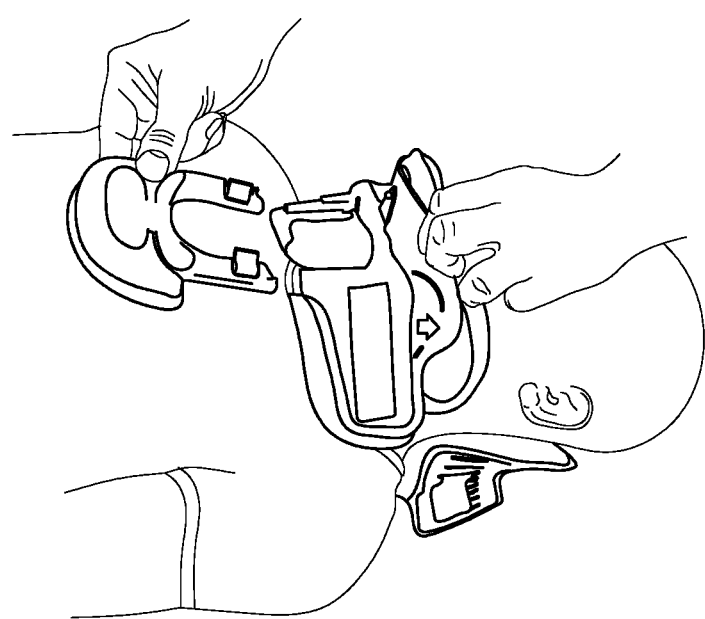
FIG. 11 shows adjusting the collar for a tracheotomy tube.

FIG. 11 shows the collar being adjusted for a tracheotomy tube. The collar can be removed without detaching a tracheotomy tube therefrom by loosening the straps and unlocking the locking buttons. The height support inclusive of the portions include the footplate can be slide from the collar down and from the front of the anterior support.

C. Conclusion

While the disclosed embodiments are designed to accommodate users having different sized anatomies, the size of the disclosed embodiments and the components can be adjusted so different users having different sized anatomical portions may benefit from the present designs.

While the disclosed embodiments of the orthopedic device are shown having discrete anterior and posterior components, the anterior and posterior components may be connected with each other along one side, and a single strap or circumferential adjustment mechanism can be provided between the anterior and posterior portions along the other side.

The overmolded edges and 3D anatomical portions, and the fold lines, living hinges, and/or slot structures, can be provided to a collar, without providing other features, such as the height adjustability, to the collar.

It is to be understood that not necessarily all objects or advantages may be achieved under any embodiment of the invention. For example, those skilled in the art will recognize that the invention may be embodied or carried out to achieve or optimizes one advantage or group of advantages as taught without achieving other objects or advantages as taught or suggested.

The skilled artisan will recognize the interchangeability of various disclosed features from different embodiments. Besides the variations described, other known equivalents for each feature can be mixed and matched by one of ordinary skill in this art to construct an orthopedic device under principles of the present invention.

Although this invention has been disclosed in certain exemplary embodiments and examples, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above.

The invention claimed is:

1. A cervical collar, comprising:
an anterior component having depending projections;
a height support adjustably securing to the anterior component, and combining therewith to form a tracheal open access area, the height support configured having first and second upright legs adapted to cooperate with the depending projections, each of the first and second upright legs includes a button manipulable to selectively lock the height support from being adjusted, each of the buttons is received in appropriately sized and shaped cut out portions of the first and second upright legs;
wherein the button includes a resilient tab arranged to engage and extend over a side portion of the corresponding upright leg to secure placement of the corresponding upright leg relative to the depending projections;
wherein a lever is formed on an opposite lateral side to the resilient tab to facilitate closing of the button, each button is rotatable about an axis defined along a height of the corresponding one of the first and second upright legs of the height support and movable in first and second opposite directions about said axis to lock or release, respectively, the button from the depending projections;
wherein a second rotatable direction of a first button of the first upright leg extends in an opposite rotatable direction as a second direction of a second button of the second upright leg, only by the first and second buttons both being rotated in the second rotatable directions can the height support adjustably be positioned relative to the anterior component.

2. The cervical collar of claim 1, wherein a tooth is formed along a reduced thickness portion of a pivot axle of the button for selective engagement with locking projections formed on the depending projections.

3. The cervical collar of claim 2, wherein the depending projections form locking projections defined as flat surfaces and each having a height spaced apart by slots along a height of the depending projections, when the button is pivoted to a disengaged, unlocked position, the tooth is removed from contacting the locking projections, and the height support can freely move up or down relative to the anterior component.

4. The cervical collar of claim 3, wherein the tooth is formed in opposition to the locking projections.

5. The cervical collar of claim 4, wherein the tooth includes a first edge having a first thickness tapering to a linear edge having a second thickness that is larger than the first thickness.

6. The cervical collar of claim 5, wherein the linear edges of the teeth engage with linear edges of the locking projections to selectively lock the height support from being adjusted to a shorter height.

7. The cervical collar of claim 1, wherein a protrusion extends from the lever and engages against a side of the corresponding upright leg.

8. The cervical collar of claim 1, wherein the height support defines a cut-away and the depending projections define indicia through which is observable the cut-away.

9. The cervical collar of claim 1, further comprising a sternal part connected at a connection to a lower end of the height support.

10. The cervical collar of claim 9, wherein the connection is non-hinged such that the connection is continuous without variations relative to the sternal part and the height support.

11. The cervical collar of claim 9, further comprising a footpad attached to the sternal part.

12. The cervical collar of claim 9, wherein the connection is rigid.

13. A method for donning a cervical collar including an anterior component and a height support adjustably securing to the anterior component and having a plurality of depending projections, and combining therewith to form a tracheal open access area, the height support including first and second buttons connecting to the anterior component on opposed first and second sides of the tracheal open access area, each of the first and second buttons including a resilient tab arranged to engage first and second sides, respectively, of the anterior component, the method comprising:
 pressing the resilient tabs of the first and second buttons whereat the first and second buttons are at a first location;
 rotating about an axis of the height support the first and second buttons in a first direction perpendicular to the axis of the height support to release the first and second buttons from the depending projections;
 sliding the height support along the anterior component from the first location and selecting a height of the tracheal open access area at a second location;
 rotating the first and second buttons in a second direction relative to the anterior component to lock the first and second buttons at the second location to the depending projections;
 wherein a second rotatable direction of a first button corresponding to a first upright leg extends in a opposite rotatable direction as a second direction of a second button corresponding to a second upright leg, only by the first and second buttons both being rotated in the second rotatable direction can the height support adjustably be positioned relative to the anterior component.

14. The method of claim 13, further comprising the step of comparing the height support to a scale located along the anterior component.

15. The method of claim 13, further comprising connecting the anterior component to a posterior component by straps securing to both the anterior and posterior components.

16. The method of claim 13, wherein the cervical collar further comprises a sternal part connected at a connection to a lower end of the height support,
 wherein the connection is non-hinged such that the connection is continuous without variations relative to the sternal part and the height support.

17. The method of claim 16, further comprising securing a footpad to the sternal part.

* * * * *